United States Patent
Volante et al.

(10) Patent No.: US 7,368,569 B2
(45) Date of Patent: May 6, 2008

(54) PROCESS FOR MAKING SPIROLACTONE COMPOUNDS

(75) Inventors: Ralph P. Volante, Cranbury, NJ (US); David M. Tschaen, Holmdel, NJ (US); Steven A. Weissman, Short Hills, NJ (US); Matthew Heileman, New Providence, NJ (US); Toshiaki Mase, Okazaki (JP); Takehiko Iida, Okazaki (JP); Kenji Maeda, Okazaki (JP); Toshihiro Wada, Tsukuba (JP); Hiroki Sato, Okazaki (JP); Kenichi Asakawa, Okazaki (JP)

(73) Assignees: Merck & Co., Inc., Rahway, NJ (US); Banyu Pharmaceutical Co., Ltd., Tokyo (JP)

( * ) Notice: Subject to any disclaimer, the term of this patent is extended or adjusted under 35 U.S.C. 154(b) by 463 days.

(21) Appl. No.: 10/531,361
(22) PCT Filed: Oct. 14, 2003
(86) PCT No.: PCT/US03/32393
§ 371 (c)(1), (2), (4) Date: Apr. 14, 2005
(87) PCT Pub. No.: WO2004/037170
PCT Pub. Date: May 6, 2004

(65) Prior Publication Data
US 2006/0014950 A1    Jan. 19, 2006

Related U.S. Application Data
(60) Provisional application No. 60/419,464, filed on Oct. 18, 2002.

(51) Int. Cl.
| C07D 405/12 | (2006.01) |
| C07D 405/14 | (2006.01) |
| C07D 307/94 | (2006.01) |
| C07D 491/107 | (2006.01) |

(52) U.S. Cl. ............ 544/230; 544/332; 544/336; 544/182; 546/15; 546/167; 548/311.4; 548/364.4; 549/265

(58) Field of Classification Search ........... 544/182, 544/231, 332, 336; 546/15, 167; 548/311.4, 548/364.4; 549/265
See application file for complete search history.

(56) References Cited

U.S. PATENT DOCUMENTS

| 6,326,375 | B1 * | 12/2001 | Fukami et al. | 514/278 |
| 6,335,345 | B1 * | 1/2002 | Fukami et al. | 514/275 |
| 6,388,077 | B1 * | 5/2002 | Fukami et al. | 546/15 |
| 6,462,053 | B1 * | 10/2002 | Fukami et al. | 514/278 |
| 6,605,720 | B1 * | 8/2003 | Maeda et al. | 546/15 |
| 6,649,624 | B2 * | 11/2003 | Fukami et al. | 514/278 |
| 6,723,847 | B2 * | 4/2004 | Fukami et al. | 544/331 |
| 6,803,372 | B2 * | 10/2004 | Fukami et al. | 514/275 |

* cited by examiner

*Primary Examiner*—Venkataraman Balasubram
(74) *Attorney, Agent, or Firm*—Baerbel R. Brown; Catherine D. Fitch

(57) ABSTRACT

This invention relates to a process for making spirolactone compounds analogous to formula I

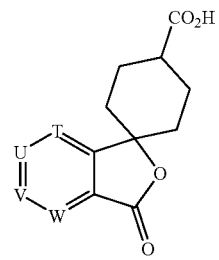

10 Claims, No Drawings

PROCESS FOR MAKING SPIROLACTONE COMPOUNDS

CROSS-REFERENCE TO RELATED APPLICATIONS

This application is a U.S. National Phase application under 35 U.S.C. §371 of PCT Application No. PCT/US2003/032393, filed Oct. 14, 2003, which claims priority under 35 U.S.C. §119 from U.S. Provisional Application No. 60/419,464, filed Oct. 18, 2002.

BACKGROUND OF THE INVENTION

The present invention further relates to a process for the preparation of the spirolactones of formula I.

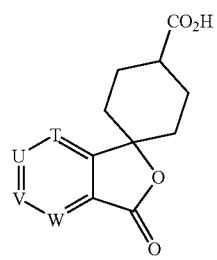

The compounds of formula I are intermediates useful for the preparation of the spirolactone compounds of formula II.

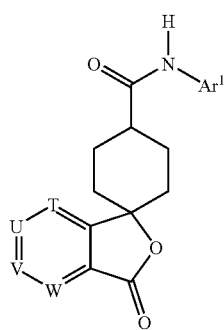

The compounds of formula II, along with their use as NPY5 antagonists for treating bulimia, obesity or diabetes, were disclosed in U.S. Pat. No. 6,335,345, which is incorporated by reference herein in its entirety, and in WO 01/14376 (published on Mar. 2, 2001). The compounds of formula II are also useful as agents for the treatment of various diseases related to NPY, including, but not limited to, cardiovascular disorders, such as hypertension, nephropathy, heart disease, vasospasm, arteriosclerosis and the like, central nervous system disorders, such as bulimia, depression, anxiety, seizure, epilepsy, dementia, pain, alcoholism, drug withdrawal and the like, metabolic diseases such as obesity, diabetes, hormone abnormality, hypercholesterolemia, hyperlipidemia and the like, sexual and reproductive dysfunction, gastrointestinal disorder, respiratory disorder, inflammation or glaucoma, and the like.

U.S. Pat. No. 6,335,345, which is incorporated by reference herein in its entirety, and WO 01/14376, describe a process for preparing the compounds of formula II from the spirolactone of formula I.

U.S. Pat. No. 6,388,077 and U.S. Ser. No. 60/352,451 describe processes for preparing the compounds of formula I. However, a large number of synthetic transformations are required (the longest linear sequence being about 7 steps) with an overall yield between about 15-20%.

With the present invention, there is produced more efficiently the compound of structural formula I in considerably fewer chemical steps utilizing fewer chemical reagents. For method A, the longest linear sequence is 4 steps with an overall yield of about 27%. For method B, the longest linear sequence is 4 steps with an overall yield of about 24%.

Processes for the preparation of organolithium reagents, 3-benzylpicolinic and 3-benzylisonicotinic acids, as well as lactone ring formation, are described in Synthetic Communications, 20 (17), pp. 2623-2629 (1990). Processes for the ortho-lithiation of N-propenylbenzamides and N-propenyl-o-toluamides are described in J. Org. Chem., vol. 57, pp. 2700-2705 (1992).

SUMMARY OF THE INVENTION

The present invention provides a process for preparing compounds of structural formula I.

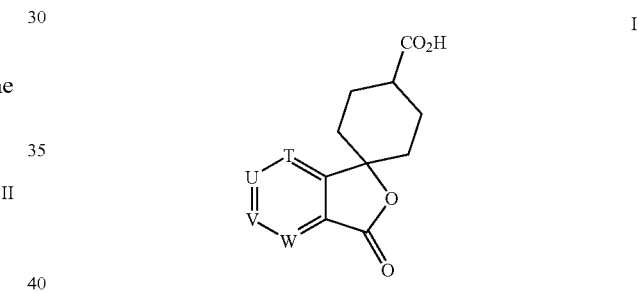

The process involves anion formation, such as ortho-lithiation, of an aromatic compound followed by the subsequent reaction with a cyclohexanone, substituted with a carboxylic acid or a carboxylic acid precursor, such as an ester, in the 4-position. After conversion of the carboxylic acid precursor into a carboxylic acid, and lactone ring formation, the desired spirolactone of formula IC is isolated in good yield. Recrystallization of spirolactone IC, or a salt thereof, and separation gives isomers IA and IB in highly pure form.

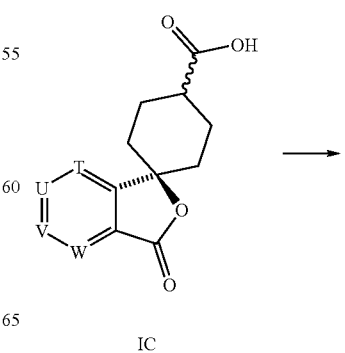

IC

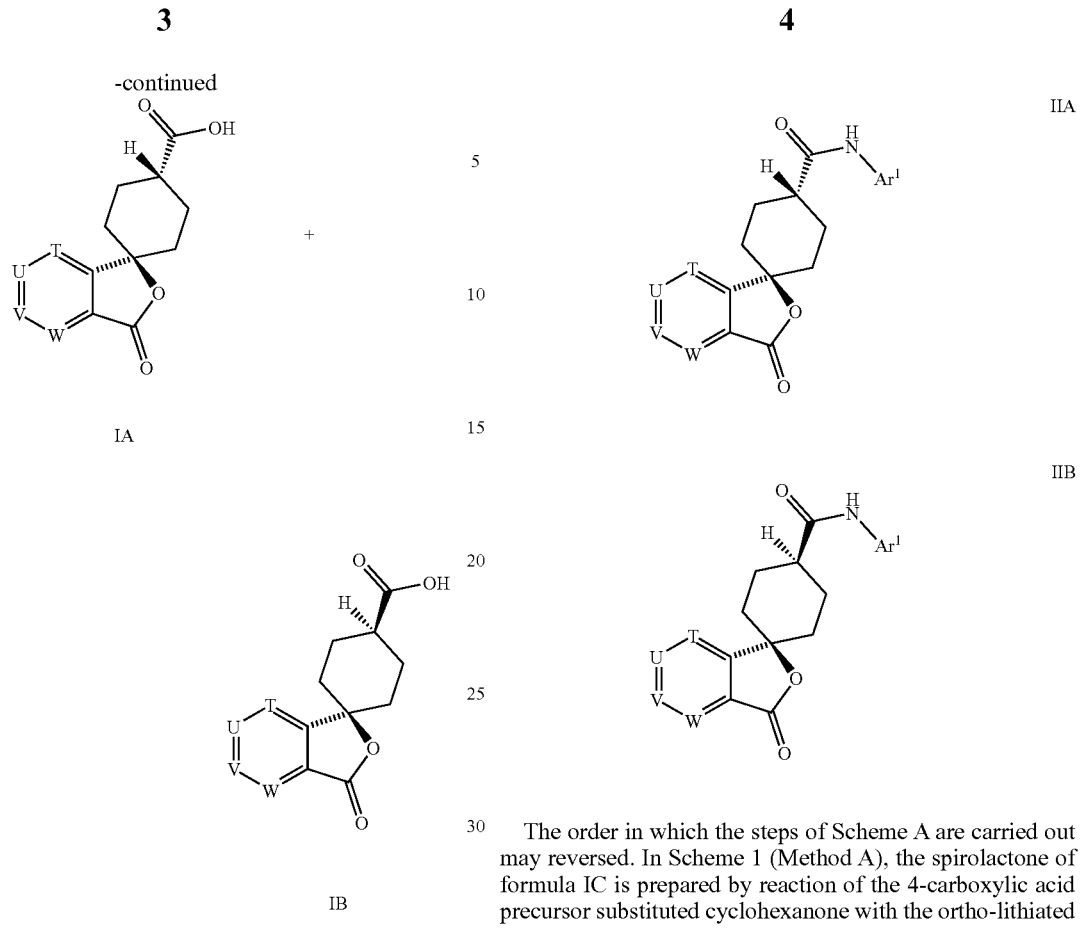

Reacting the spirolactone I with an amine of the formula $H_2NAr^1$ gives spirolactone amides of general structural formula I as shown in Scheme A. Reacting the separated spirolactone of formula IA or IB with an amine of the formula $H_2NAr^1$ gives corresponding spirolactone amide IIA or IIB.

The order in which the steps of Scheme A are carried out may reversed. In Scheme 1 (Method A), the spirolactone of formula IC is prepared by reaction of the 4-carboxylic acid precursor substituted cyclohexanone with the ortho-lithiated aromatic compound, followed by conversion of the acid precursor into a carboxylic acid, and subsequent lactone ring formation. Alternatively, in Scheme 2 (Method B), the reaction of the 4-carboxylic acid precursor substituted cyclohexanone with the ortho-lithiated aromatic compound is followed by lactone ring formation, and the subsequent conversion of the carboxylic acid precursor into a carboxylic acid to form the spirolactone of formula IA.

Scheme A

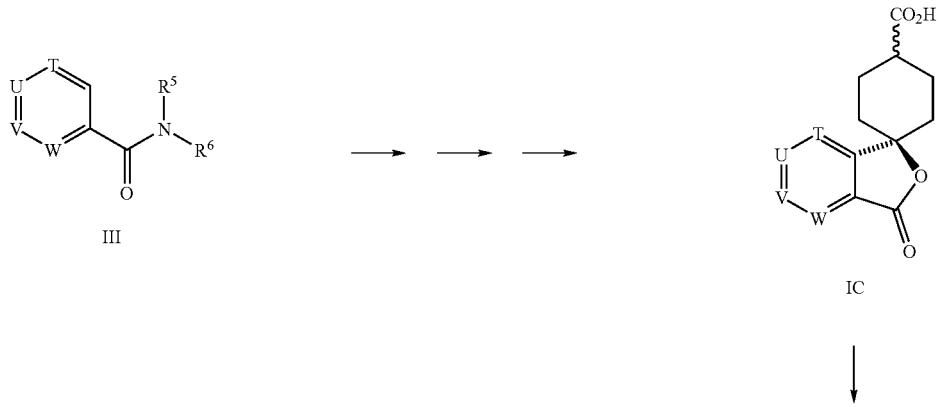

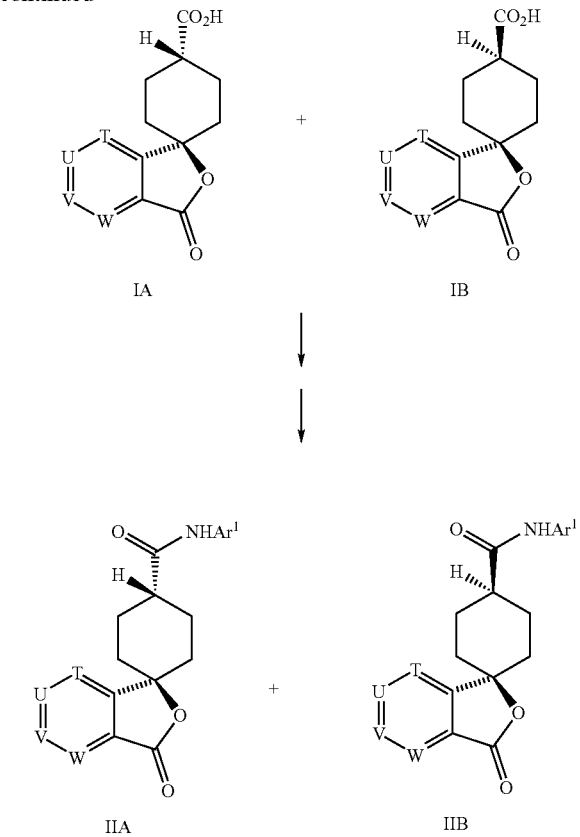

DETAILED DESCRIPTION OF THE INVENTION

By this invention, there is provided a process for the preparation of a compound of structural formula I, or a salt thereof

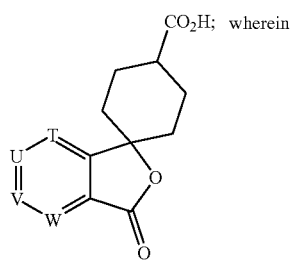

T, U, V and W are each independently selected from the group consisting of
(1) nitrogen, and
(2) methine,
wherein the methine group is unsubstituted or optionally substituted with a substituent selected from the group consisting of
(a) halogen,
(b) lower alkyl,
(c) hydroxy, and
(d) lower alkoxy, and wherein at least two of T, U, V, and W are methine;
comprising the steps of
(a) combining a strong base with a compound of formula III

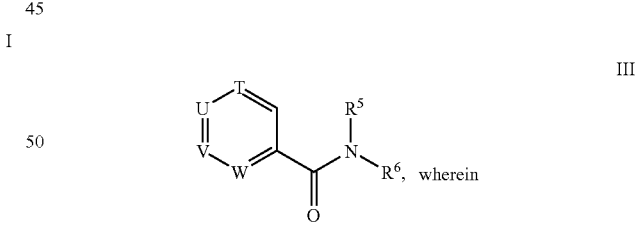

$R^5$ and $R^6$ are independently selected from the group consisting of
(1) hydrogen,
(2) lower alkyl,
(3) cycloalkyl,
(4) cycloheteroalkyl,
(5) aryl, and
(6) heteroaryl,
in an aprotic solvent to form a solution;
(b) reacting a cyclohexanone of formula IV with the solution of step (a)

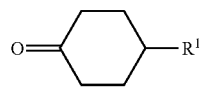

IV wherein $R^1$ is selected from the group consisting of
(1) —$CO_2H$,
(2) —CN,
(3) —$CH_2OH$,
(4) aryl,
(5) ester,
(6) protected carboxylic acid, and
(7) a ketal selected from the group consisting of

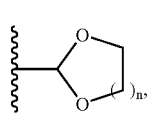 and (b) 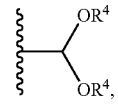

wherein n is 1 or 2, and $R^4$ is lower alkyl;
(c) converting the $R^1$ substituent of the cyclohexanone of step (b) into a carboxylic acid when $R^1$ is not a carboxylic acid; and
(d) adding an acid to form a spirolactone;
to afford the compound I, or a salt thereof.

In one embodiment of the present invention, the $R^1$ substituent of step (b) is selected from the group consisting of
(1) —$CO_2H$,
(2) —CN,
(3) —$CH_2OH$,
(4) phenyl,
(5) —$CO_2R^2$, wherein $R^2$ is selected from the group consisting of:
   (a) lower alkyl, and
   (b) —$CH_2$-phenyl, wherein the phenyl group is unsubstituted or substituted with a substituent selected from the group consisting of:
      (1) lower alkyl,
      (2) lower alkoxy, and
      (3) —$NO_2$,
(6) —C(O)$NHR^3$, wherein $R^3$ is lower alkyl,
(7) —C(O)N($R^3$)$_2$, wherein $R^3$ is lower alkyl,
(8) —(CO)$NH_2NH_2$, and
(9) a ketal selected from the group consisting of

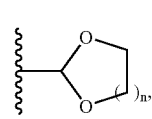 and (b) 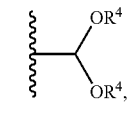

wherein n is 1 or 2, and $R^4$ is lower alkyl.

In a class of this embodiment, $R^1$ is —$CO_2R^2$, wherein $R^2$ is selected from the group consisting of:
(a) lower alkyl, and
(b) —$CH_2$-phenyl, wherein the phenyl group is unsubstituted or substituted with a substituent selected from the group consisting of:
(1) lower alkyl,
(2) lower alkoxy, and
(3) —$NO_2$.

In another embodiment of the present invention, T, V and W are methine, wherein the methine group is unsubstituted or optionally substituted with a substituent selected from the group consisting of
(a) halogen,
(b) lower alkyl,
(c) hydroxy, and
(d) lower alkoxy; and U is nitrogen.

In a class of this embodiment, T, V and W are unsubstituted methine; and U is nitrogen.

In another embodiment of the present invention, T, U, V and W are methine, wherein the methine group is unsubstituted or optionally substituted with a substituent selected from the group consisting of
(a) halogen,
(b) lower alkyl,
(c) hydroxy, and
(d) lower alkoxy.

In one class of this embodiment, the methine group is unsubstituted or optionally substituted with halogen.

In another embodiment of this invention, the process further comprises the step (e) of isolating the compound of formula I.

By this invention, there is further provided a process for the preparation of a compound of structural formula IC, or a salt thereof,

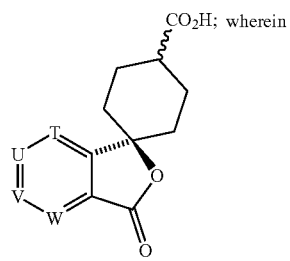

IC

T, U, V and W are each independently selected from the group consisting of
(1) nitrogen, and
(2) methine,
   wherein the methine group is unsubstituted or optionally substituted with a substituent selected from the group consisting of
   (a) halogen,
   (b) lower alkyl,
   (c) hydroxy, and
   (d) lower alkoxy, and wherein at least two of T, U, V, and W are methine;
comprising the steps of
(a) combining a strong base with a compound of formula A

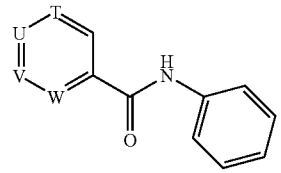

A in an aprotic solvent to form a solution;

(b) reacting a compound of formula B

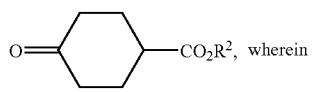, wherein

R² is selected from the group consisting of:
(a) lower alkyl, and
(b) —CH₂-phenyl, wherein the phenyl group is unsubstituted or substituted with a substituent selected from the group consisting of
(1) lower alkyl,
(2) lower alkoxy, and
(3) —NO₂,
with the solution of step (a) to form a solution;
(c) reacting the solution of step (b) with water to form a solution; and
(d) adjusting the pH of the solution of step (c) to between about 0 and 4 with an acid to afford the compound IC, or a salt thereof.

In one embodiment of the present invention, T, V and W are methine, wherein the methine group is unsubstituted or optionally substituted with a substituent selected from the group consisting of
(a) halogen,
(b) lower alkyl,
(c) hydroxy, and
(d) lower alkoxy; and U is nitrogen.

In a class of this embodiment, T, V and W are unsubstituted methine; and U is nitrogen.

In another embodiment of the present invention, T, U, V and W are methine, wherein the methine group is unsubstituted or optionally substituted with a substituent selected from the group consisting of
(a) halogen,
(b) lower alkyl,
(c) hydroxy, and
(d) lower alkoxy.

In one class of this embodiment, the methine group is unsubstituted or optionally substituted with halogen.

In another embodiment of the present invention, steps (a) and (b) are run at a temperature of between about −50° C. and −80° C. In a class of this embodiment, step (a) is aged at a temperature less than about −55° C. In a subclass of this class, step (a) is aged for a period between about 5 minutes to 18 hours.

In another embodiment of this invention, the aprotic solvent of step (a) is selected from the group consisting of tetrahydrofuran, toluene, heptane, dimethoxyethane, benzene, and hexane, diethyl ether, xylene, or a mixture thereof. In a class of this embodiment, the aprotic solvent of step (a) is tetrahydrofuran.

In another embodiment of this invention, the strong base of step (a) is selected from the group consisting of n-BuLi, sec-BuLi, t-BuLi, LiHMDS, NaHMDS, KHMDS and LiTMP. In a class of this embodiment, the strong base of step (a) is n-BuLi.

In another embodiment of this invention, step (a) further comprises adding a salt selected from the group consisting of LiBr, LiCl, LiI, LiBF₄, LiClO₄, and CeCl₃. In a class of this embodiment, the salt of step (a) is LiBr.

In another embodiment of this invention, R² is selected from the group consisting of: —CH₃, —CH₂CH₃, —(CH₂)₂ CH₃, —CH(CH₃)₂, —(CH₂)₃CH₃, and —CH(CH₃)₃. In a class of this embodiment, R² is —CH₂CH₃.

In another embodiment of the present invention, step (c) is run at a temperature between about 0° C. to 50° C. In a class of this embodiment, step (c) is run at a temperature of about 40° C. In a subclass of this class, step (c) is run for a period between about 1 hour to 4 hours.

In another embodiment of this invention, the acid of step (d) is selected from the group consisting of hydrochloric acid, sulfuric acid, methane sulfonic acid, trifluoromethane sulfonic acid, or a mixture thereof. In a class of this embodiment, the acid of step (d) is sulfuric acid.

In another embodiment of this invention, the acid of step (d) is selected from the group consisting of hydrochloric acid, sulfuric acid, methane sulfonic acid, trifluoromethane sulfonic acid, p-toluene sulfonic acid, benzene sulfonic acid, or a mixture thereof.

In another embodiment of this invention, the acid of step (d) is an aqueous acid selected from the group consisting of hydrochloric acid, sulfuric acid, methane sulfonic acid, trifluoromethane sulfonic acid, or a mixture thereof. In a class of this embodiment, the aqueous acid of step (d) is sulfuric acid.

In another embodiment of this invention, the acid of step (d) is an aqueous acid selected from the group consisting of hydrochloric acid, sulfuric acid, methane sulfonic acid, trifluoromethane sulfonic acid, p-toluene sulfonic acid, benzene sulfonic acid, or a mixture thereof.

In another embodiment of the present invention, the pH of step (d) is adjusted to between about 1 to 3.

In another embodiment of the present invention, step (d) is aged at a temperature between about 30° C. to 70° C. In a class of this embodiment, step (d) is aged at a temperature of about 40° C. In a subclass of this class, step (d) is aged for between about 30 minutes to 4 hours.

In another embodiment of this invention, the process further comprises the step (e) of isolating the compound of formula IC, or a salt thereof.

By this invention, there is further provided a process for the preparation of a compound of structural formula IC, or a salt thereof,

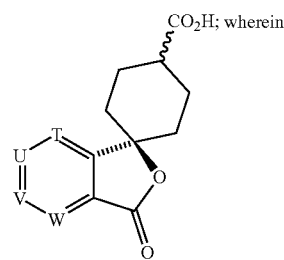

T, U, V and W are each independently selected from the group consisting of
(1) nitrogen, and
(2) methine,
wherein the methine group is unsubstituted or optionally substituted with a substituent selected from the group consisting of
(a) halogen,
(b) lower alkyl,
(c) hydroxy, and
(d) lower alkoxy, and wherein at least two of T, U, V, and W are methine;

comprising the step of adjusting the pH of a solution of compound C

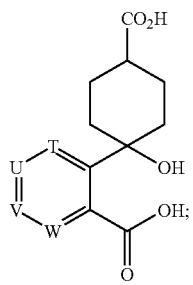

in a solvent to a pH between about 0 and 4 with an acid to afford the compound IC, or a salt thereof.

In one embodiment of the present invention, T, V and W are methine, wherein the methine group is unsubstituted or optionally substituted with a substituent selected from the group consisting of
(a) halogen,
(b) lower alkyl,
(c) hydroxy, and
(d) lower alkoxy; and U is nitrogen.

In a class of this embodiment, T, V and W are unsubstituted methine; and U is nitrogen.

In another embodiment of the present invention, T, U, V and W are methine, wherein the methine group is unsubstituted or optionally substituted with a substituent selected from the group consisting of
(a) halogen,
(b) lower alkyl,
(c) hydroxy, and
(d) lower alkoxy.

In one class of this embodiment, the methine group is unsubstituted or optionally substituted with halogen.

In another embodiment of this invention, the solvent is selected from the group consisting of tetrahydrofuran, toluene, heptane, dimethoxyethane, benzene, and hexane, diethyl ether, xylene, water, or a mixture thereof. In one class of this embodiment, the solvent is selected from the group consisting of tetrahydrofuran and water, or a mixture thereof.

In another embodiment of this invention, the acid is selected from the group consisting of hydrochloric acid, sulfuric acid, methane sulfonic acid, trifluoromethane sulfonic acid, or a mixture thereof. In a class of this embodiment, the acid is sulfuric acid.

In another embodiment of this invention, the acid is selected from the group consisting of hydrochloric acid, sulfuric acid, methane sulfonic acid, trifluoromethane sulfonic acid, p-toluene sulfonic acid, benzene sulfonic acid, or a mixture thereof.

In another embodiment of this invention, the acid is an aqueous acid selected from the group consisting of hydrochloric acid, sulfuric acid, methane sulfonic acid, trifluoromethane sulfonic acid, or a mixture thereof. In a class of this embodiment, the aqueous acid is sulfuric acid.

In another embodiment of this invention, the acid is an aqueous acid selected from the group consisting of hydrochloric acid, sulfuric acid, methane sulfonic acid, trifluoromethane sulfonic acid, p-toluene sulfonic acid, benzene sulfonic acid, or a mixture thereof.

In another embodiment of the present invention, the pH is adjusted to between about 1 to 3.

In another embodiment of the present invention, the solution is aged at a temperature between about 30° C. to 70° C. In a class of this embodiment, the solution is aged at a temperature of about 40° C. In a subclass of this class, the solution is aged for between about 30 minutes to 4 hours.

In another embodiment of this invention, the process further comprises the step of isolating the compound of formula IC, or a salt thereof.

By this invention, there is further provided a process for the preparation and separation of a spirolactone of formula IA, or a salt thereof, and a spirolactone of formula IB, or a salt thereof,

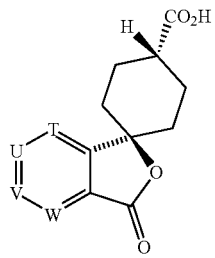

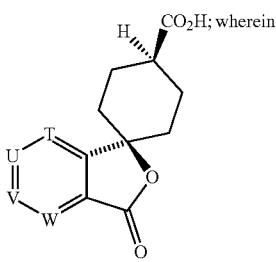

T, U, V and W are each independently selected from the group consisting of
(1) nitrogen, and
(2) methine,
wherein the methine group is unsubstituted or optionally substituted with a substituent selected from the group consisting of
(a) halogen,
(b) lower alkyl,
(c) hydroxy, and
(d) lower alkoxy, and
wherein at least two of T, U, V, and W are methine;

comprising the steps of
(f) adding an aprotic solvent to the compound of formula IC, or a salt thereof,

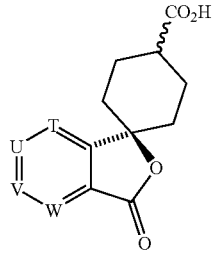

to form a mixture; and (g) aging the mixture of step (f) for a time and under conditions effective to afford the compound IA, or a salt thereof

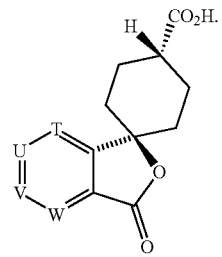

In one embodiment of the present invention, T, V and W are methine, wherein the methine group is unsubstituted or optionally substituted with a substituent selected from the group consisting of
(a) halogen,
(b) lower alkyl,
(c) hydroxy, and
(d) lower alkoxy; and U is nitrogen.

In a class of this embodiment, T, V and W are unsubstituted methine; and U is nitrogen.

In another embodiment of the present invention, T, U, V and W are methine, wherein the methine group is unsubstituted or optionally substituted with a substituent selected from the group consisting of
(a) halogen,
(b) lower alkyl,
(c) hydroxy, and
(d) lower alkoxy.

In one class of this embodiment, the methine group is unsubstituted or optionally substituted with halogen.

In another embodiment of this invention, the aprotic solvent of step (f) is selected from the group consisting of tetrahydrofuran, ethyl acetate, methyl t-butyl ether, toluene, or a mixture thereof.

In another embodiment of this invention, step (f) further comprises adding an acid to the mixture of step (f). In a class of this embodiment, the acid of step (f) is selected from the group consisting of hydrochloric acid, hydrobromic acid, tartaric acid, methane sulfonic acid, toluene sulfonic acid, succinic acid, and sulfuric acid. In a subclass of this class, the acid of step (f) is hydrochloric acid. In another class of this embodiment, the acid of step (f) is selected from the group consisting of hydrochloric acid, hydrobromic acid, tartaric acid, methane sulfonic acid, toluene sulfonic acid, succinic acid, benzene sulfonic acid, and sulfuric acid.

In another embodiment of this invention, the step (g) is aged at a temperature of about 40° C. to 60° C. In a class of this embodiment, step (g) is aged for a period between about 1 hour to about 48 hours.

In another embodiment of this invention, the process further comprises step (h) of isolating the compound of formula IA, or a salt thereof.

By this invention, there is also provided a process for the preparation of the compound of structural formula IA, or a salt thereof,

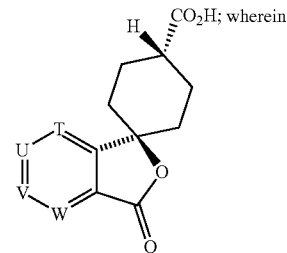

T, U, V and W are each independently selected from the group consisting of
(1) nitrogen, and
(2) methine,
wherein the methine group is unsubstituted or optionally substituted with a substituent selected from the group consisting of
(a) halogen,
(b) lower alkyl,
(c) hydroxy, and
(d) lower alkoxy, and
wherein at least two of T, U, V, and W are methine;
comprising the steps of
(a) combining a strong base with a compound of formula A

in an aprotic solvent to form a solution;
(b) reacting a compound of formula B

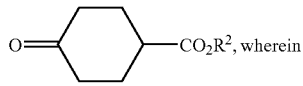

$R^2$ is selected from the group consisting of:
(a) lower alkyl, and
(b) —$CH_2$-phenyl, wherein the phenyl group is unsubstituted or substituted with a substituent selected from the group consisting of
(1) lower alkyl,
(2) lower alkoxy, and
(3) —$NO_2$,
with the solution of step (a) to form a solution;
(c) adjusting the pH of the solution of step (b) to between about 0 and 4 with an acid to form a compound of formula E

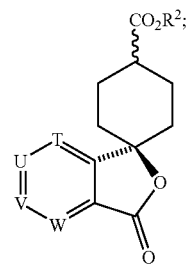

(d) contacting the compound of formula E of step (c), wherein at least one of T, U, V and W is nitrogen, with an acid to form a salt of compound E; and (e) treating compound E, or a salt thereof, with an acid to form a salt of compound IA.

In one embodiment of the present invention, T, V and W are methine, wherein the methine group is unsubstituted or optionally substituted with a substituent selected from the group consisting of (a) halogen,
(b) lower alkyl,
(c) hydroxy, and
(d) lower alkoxy; and U is nitrogen.

In a class of this embodiment, T, V and W are unsubstituted methine; and U is nitrogen.

In another embodiment of the present invention, T, U, V and W are methine, wherein the methine group is unsubstituted or optionally substituted with a substituent selected from the group consisting of (a) halogen,
(b) lower alkyl,
(c) hydroxy, and
(d) lower alkoxy.

In one class of this embodiment, the methine group is unsubstituted or optionally substituted with halogen.

In another embodiment of the present invention, the steps (a) and (b) are run at a temperature of between about −50° C. and −80° C. In a class of this embodiment, step (a) is aged at a temperature less than about −55° C. In a subclass of this class, step (a) is aged for a period between about 5 minutes to 18 hours.

In another embodiment of this invention, step (b) is aged at a temperature less than about −55° C. In a class of this embodiment, step (b) is aged for a period between about 1 hour to 12 hours.

In another embodiment of this invention, the aprotic solvent of step (a) is selected from the group consisting of tetrahydrofuran, toluene, heptane, dimethoxyethane, benzene, and hexane, diethyl ether, xylene, or a mixture thereof. In a class of this embodiment, the aprotic solvent of step (a) is tetrahydrofuran.

In another embodiment of this invention, the strong base of step (a) is selected from the group consisting of n-BuLi, sec-BuLi, t-BuLi, LiHMDS, NaHMDS, KHMDS and LiTMP. In a class of this embodiment, the strong base of step (a) is n-BuLi.

In another embodiment of this invention, step (a) further comprises adding a salt selected from the group consisting of LiBr, LiCl, LiI, LiBF$_4$, LiClO$_4$, and CeCl$_3$. In a class of this embodiment, the salt of step (a) is LiBr.

In another embodiment of this invention, the acid of step (c) is selected from the group consisting of camphor sulfonic acid, sulfuric acid, hydrochloric acid, methane sulfonic acid, acetic acid, trifluoromethane sulfonic acid, or a mixture thereof. In a class of this embodiment, the acid of step (c) is acetic acid.

In another embodiment of this invention, the acid of step (c) is selected from the group consisting of camphor sulfonic acid, sulfuric acid, hydrochloric acid, methane sulfonic acid, acetic acid, trifluoromethane sulfonic acid, p-toluene sulfonic acid, benzene sulfonic acid, or a mixture thereof.

In another embodiment of this invention, step (c) further comprises adding a solvent selected from the group consisting of $C_{1-6}$ alcohol, tetrahydrofuran and toluene. In a class of this embodiment, the solvent is selected from methanol, ethanol, propanol, isopropanol, butanol, t-butanol and sec-butanol. In a subclass of this class, the solvent is ethanol.

In another embodiment of this invention, step (c) is run at a temperature between about 20° C. to 60° C. In a class of this embodiment, step (c) is aged for 30 minutes to 2 days.

In another embodiment of this invention, the pH of step (c) is adjusted to less than or equal to 5.

In another embodiment of this invention, the acid of step (d) is selected from the group consisting of camphor sulfonic acid, sulfuric acid, hydrochloric acid, methane sulfonic acid, trifluoromethane sulfonic acid, or a mixture thereof. In a class of this embodiment, the acid of step (d) is camphor sulfonic acid.

In another embodiment of this invention, the acid of step (d) is selected from the group consisting of camphor sulfonic acid, sulfuric acid, hydrochloric acid, methane sulfonic acid, trifluoromethane sulfonic acid, p-toluene sulfonic acid, benzene sulfonic acid, or a mixture thereof.

In another embodiment of this invention, the temperature of step (d) is between about ambient temperature and 80° C. to form a salt. In a class of this embodiment, step (d) is heated to a temperature of between about 50° C. to 80° C. to form the salt.

In another embodiment of this invention, $R^2$ is selected from the group consisting of: —$CH_3$, —$CH_2CH_3$, —$(CH_2)_2CH_3$, —$CH(CH_3)_2$, —$(CH_2)_3CH_3$, and —$CH(CH_3)_3$. In a class of this embodiment, $R^2$ is —$CH_2CH_3$.

In another embodiment of this invention, the acid of step (e) is selected from the group consisting of hydrochloric acid, sulfuric acid, methane sulfonic acid, trifluoromethane sulfonic acid, or a mixture thereof. In a subclass of this class, the acid of step (e) is sulfuric acid.

In another embodiment of this invention, the acid of step (e) is selected from the group consisting of hydrochloric acid, sulfuric acid, methane sulfonic acid, trifluoromethane sulfonic acid, p-toluene sulfonic acid, benzene sulfonic acid, or a mixture thereof.

In another embodiment of this invention, the acid of step (e) is an aqueous acid selected from the group consisting of hydrochloric acid, sulfuric acid, methane sulfonic acid, trifluoromethane sulfonic acid, or a mixture thereof. In a subclass of this class, the aqueous acid of step (e) is sulfuric acid.

In another embodiment of this invention, the acid of step (e) is an aqueous acid selected from the group consisting of hydrochloric acid, sulfuric acid, methane sulfonic acid, trifluoromethane sulfonic acid, p-toluene sulfonic acid, benzene sulfonic acid, or a mixture thereof.

In another embodiment of this invention, the pH of step (e) is between about 0 to 4. In a class of this embodiment, the pH of step (e) is between about 2 to 4.

In another class of this embodiment, the temperature of step (e) is between about 50° C. and 100° C.

In one embodiment of the present invention, the process further comprises the step (f) of treating the salt of compound IA with a base to form the free acid IA in solution. In one class of this embodiment, the base of step (f) is selected from a group consisting of sodium hydroxide, potassium hydroxide, potassium carbonate, sodium carbonate, and sodium bicarbonate. In a subclass of this class, the base of step (f) is sodium hydroxide. In another class of this embodiment, the pH of the solution step (f) is between about 2 to 4.

In another embodiment of the present invention, the process further comprises the step (g) of isolating compound IA.

By this invention, there is also provided a process for the preparation of the compound of structural formula IA, or a salt thereof,

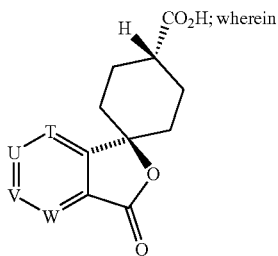

T, U, V and W are each independently selected from the group consisting of
(1) nitrogen, and
(2) methine,
wherein the methine group is unsubstituted or optionally substituted with a substituent selected from the group consisting of
(a) halogen,
(b) lower alkyl,
(c) hydroxy, and
(d) lower alkoxy, and
wherein at least two of T, U, V, and W are methine, comprising the steps of
(a) contacting the compound of formula E

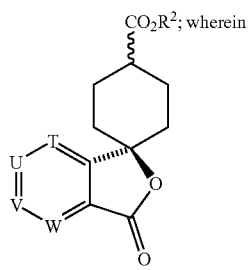

$R^2$ is selected from the group consisting of:
(a) lower alkyl, and
(b) —$CH_2$-phenyl, wherein the phenyl group is unsubstituted or substituted with a substituent selected from the group consisting of
(1) lower alkyl,
(2) lower alkoxy, and
(3) —$NO_2$, and
wherein at least one of T, U, V and W is nitrogen, with an acid to form a salt of compound E; and
(b) treating compound E, or a salt thereof, with an acid to form compound IA, or a salt thereof.

In one embodiment of the present invention, T, V and W are methine, wherein the methine group is unsubstituted or optionally substituted with a substituent selected from the group consisting of
(a) halogen,
(b) lower alkyl,
(c) hydroxy, and
(d) lower alkoxy; and U is nitrogen.
In a class of this embodiment, T, V and W are unsubstituted methine; and U is nitrogen.

In another embodiment of the present invention, T, U, V and W are methine, wherein the methine group is unsubstituted or optionally substituted with a substituent selected from the group consisting of
(a) halogen,
(b) lower alkyl,
(c) hydroxy, and
(d) lower alkoxy.
In one class of this embodiment, the methine group is unsubstituted or optionally substituted with halogen.

In another embodiment of this invention, step (a) further comprises adding a solvent selected from the group consisting of $C_{1-6}$ alcohol, tetrahydrofuran and toluene. In a class of this embodiment, the solvent is selected from methanol, ethanol, propanol, isopropanol, butanol, t-butanol and sec-butanol. In a subclass of this class, the solvent is ethanol.

In another embodiment of this invention, the acid of step (a) is selected from the group consisting of camphor sulfonic acid, sulfuric acid, hydrochloric acid, methane sulfonic acid, trifluoromethane sulfonic acid, or a mixture thereof. In a class of this embodiment, the acid of step (a) is camphor sulfonic acid.

In another embodiment of this invention, the acid of step (a) is selected from the group consisting of camphor sulfonic acid, sulfuric acid, hydrochloric acid, methane sulfonic acid, trifluoromethane sulfonic acid, p-toluene sulfonic acid, benzene sulfonic acid, or a mixture thereof.

In another embodiment of this invention, the temperature of step (a) is between about ambient temperature and 80° C. to form a salt. In a class of this embodiment, step (a) is heated to a temperature of between about 50° C. to 80° C. to form the salt.

In another embodiment of this invention, $R^2$ is selected from the group consisting of: —$CH_3$, —$CH_2CH_3$, —$(CH_2)_2CH_3$, —$CH(CH_3)_2$, —$(CH_2)_3CH_3$, and —$CH(CH_3)_3$. In a class of this embodiment, $R^2$ is —$CH_2CH_3$.

In another embodiment of this invention, the acid of step (b) is selected from the group consisting of hydrochloric acid, sulfuric acid, methane sulfonic acid, trifluoromethane sulfonic acid, or a mixture thereof. In a subclass of this class, the acid of step (b) is sulfuric acid.

In another embodiment of this invention, the acid of step (b) is selected from the group consisting of hydrochloric acid, sulfuric acid, methane sulfonic acid, trifluoromethane sulfonic acid, p-toluene sulfonic acid, benzene sulfonic acid, or a mixture thereof.

In another embodiment of this invention, the acid of step (b) is an aqueous acid selected from the group consisting of hydrochloric acid, sulfuric acid, methane sulfonic acid, trifluoromethane sulfonic acid, or a mixture thereof. In a subclass of this class, the aqueous acid of step (b) is sulfuric acid.

In another embodiment of this invention, the acid of step (b) is an aqueous acid selected from the group consisting of hydrochloric acid, sulfuric acid, methane sulfonic acid, trifluoromethane sulfonic acid, p-toluene sulfonic acid, benzene sulfonic acid, or a mixture thereof.

In another embodiment of this invention, the pH of step (b) is between about 0 to 4. In a class of this embodiment, the pH of step (b) is between about 2 to 4.

In another class of this embodiment, the temperature of step (b) is between about 50° C. and 100° C.

In another embodiment of the present invention, the process further comprises the step (c) of isolating compound IA, or a salt thereof.

By this invention, there is also provided a process for preparing a compound of formula IA, or a salt thereof,

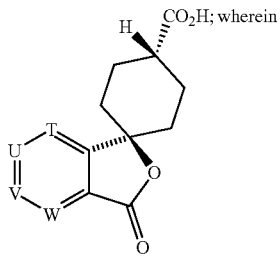

IA

T, U, V and W are each independently selected from the group consisting of
  (1) nitrogen, and
  (2) methine,
    wherein the methine group is unsubstituted or optionally substituted with a substituent selected from the group consisting of
    (a) halogen,
    (b) lower alkyl,
    (c) hydroxy, and
    (d) lower alkoxy, and
    wherein at least two of T, U, V, and W are methine;

comprising the steps of
  (a) adding an aprotic solvent to the compound of formula IC, or a salt thereof,

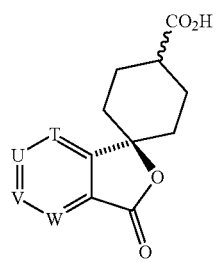

IC to form a mixture; and
  (b) aging the mixture of step (a) for a time and under conditions effective to afford the compound IA, or a salt thereof.

In one embodiment of the present invention, T, V and W are methine, wherein the methine group is unsubstituted or optionally substituted with a substituent selected from the group consisting of
  (a) halogen,
  (b) lower alkyl,
  (c) hydroxy, and
  (d) lower alkoxy; and
U is nitrogen.

In a class of this embodiment, T, V and W are unsubstituted methine; and U is nitrogen.

In another embodiment of the present invention, T, U, V and W are methine, wherein the methine group is unsubstituted or optionally substituted with a substituent selected from the group consisting of
  (a) halogen,
  (b) lower alkyl,
  (c) hydroxy, and
  (d) lower alkoxy.

In one class of this embodiment, the methine group is unsubstituted or optionally substituted with halogen.

In another embodiment of this invention, the aprotic solvent of step (a) is selected from the group consisting of tetrahydrofuran, ethyl acetate, methyl t-butyl ether, toluene, or a mixture thereof.

In another embodiment of this invention, step (a) further comprises adding an acid to the mixture of step (a). In a class of this embodiment, the acid of step (a) is selected from the group consisting of hydrochloric acid, hydrobromic acid, tartaric acid, methane sulfonic acid, toluene sulfonic acid, succinic acid, benzene sulfonic acid and sulfuric acid. In a subclass of this class, the acid of step (a) is hydrochloric acid.

In another embodiment of this invention, the step (b) is aged at a temperature of about 40° C. to 60° C. In a class of this embodiment, step (b) is aged for a period between about 1 hour to about 48 hours.

By this invention, there is also provided a compound of structural formula C, or a salt thereof,

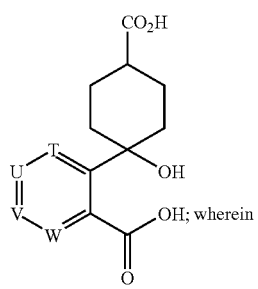

C

T, U, V and W are each independently selected from the group consisting of
  (1) nitrogen, and
  (2) methine,
    wherein the methine group is unsubstituted or optionally substituted with a substituent selected from the group consisting of
    (a) halogen,
    (b) lower alkyl,
    (c) hydroxy, and
    (d) lower alkoxy, and
  wherein at least two of T, U, V, and W are methine.

In another embodiment of the present invention, T, V and W are methine, wherein the methine group is unsubstituted or optionally substituted with a substituent selected from the group consisting of
  (a) halogen,
  (b) lower alkyl,
  (c) hydroxy, and
  (d) lower alkoxy; and
U is nitrogen.

In one class of this embodiment, T, V and W are unsubstituted methine; and U is nitrogen.

In another class of this embodiment, there is provided a compound of structural formula 1-3 or a salt thereof.

In another embodiment of the present invention, T, U, V and W are methine, wherein the methine group is unsubstituted or optionally substituted with a substituent selected from the group consisting of
(a) halogen,
(b) lower alkyl,
(c) hydroxy, and
(d) lower alkoxy.

In one class of this embodiment, the methine group is unsubstituted or optionally substituted with halogen.

By this invention, there is also provided a compound of structural formula E, or a salt thereof, T, U, V and W are each independently selected from the group consisting of
(1) nitrogen, and
(2) methine,
wherein the methine group is unsubstituted or optionally substituted with a substituent selected from the group consisting of
(a) halogen,
(b) lower alkyl,
(c) hydroxy, and
(d) lower alkoxy, and wherein at least two of T, U, V, and W are methine; and $R^2$ is selected from the group consisting of:
(a) lower alkyl, and
(b) —$CH_2$-phenyl, wherein the phenyl group is unsubstituted or substituted with a substituent selected from the group consisting of:
(1) lower alkyl,
(2) lower alkoxy, and
(3) —$NO_2$.

In one embodiment of this invention, $R^2$ is selected from the group consisting of: —$CH_3$, —$CH_2CH_3$, —$(CH_2)_2CH_3$, —$CH(CH_3)_2$, —$(CH_2)_3$, and —$CH(CH_3)_3$. In a class of this embodiment, $R^2$ is —$CH_2CH_3$.

In another embodiment of the present invention, T, V and W are methine, wherein the methine group is unsubstituted or optionally substituted with a substituent selected from the group consisting of
(a) halogen,
(b) lower alkyl,
(c) hydroxy, and
(d) lower alkoxy; and U is nitrogen.

In one class of this embodiment, T, V and W are unsubstituted methine; and U is nitrogen.

In another class of this embodiment, there is provided a compound of structural formula 2-3 or a salt thereof.

In another embodiment of the present invention, T, U, V and W are methine, wherein the methine group is unsubstituted or optionally substituted with a substituent selected from the group consisting of
(a) halogen,
(b) lower alkyl,
(c) hydroxy, and
(d) lower alkoxy.

In one class of this embodiment, the methine group is unsubstituted or optionally substituted with halogen.

As used herein "T, U, V and W" refer to a nitrogen or a methine, wherein the methine group is unsubstituted or optionally substituted with a substituent selected from the group consisting of halogen, lower alkyl, hydroxy, and lower alkoxy, and wherein at least two of T, U, V, and W are methine.

"Methine group is unsubstituted or optionally substituted with a substituent selected from the group consisting of halogen, lower alkyl, hydroxy and lower alkoxy" refers to unsubstituted methine or methine having a substituent which can be selected from the group consisting of halogen, lower alkyl, hydroxy and lower alkoxy. The aforesaid substituent includes preferably halogen, and the like.

"Halogen" or "halide" refers to fluorine atom, chlorine atom, bromine atom and iodine atom. Halogen atom as the aforesaid substituent includes preferably fluorine atom, chlorine atom, and the like.

"Lower alkyl" refers to a straight- or branched-chain alkyl group of $C_1$ to $C_6$, for example, methyl, ethyl, propyl, isopropyl, butyl, isobutyl, sec-butyl, tert-butyl, pentyl, isopentyl, hexyl, isohexyl, and the like. Lower alkyl as the aforesaid substituent includes preferably methyl, ethyl, and the like.

"Lower alkoxy" refers to a straight- or branched-chain alkoxy group of $C_1$ to $C_6$, for example, methoxy, ethoxy, propoxy, isopropoxy, butoxy, sec-butoxy, isobutoxy, tert-butoxy, pentyloxy, isopentyloxy, hexyloxy, isohexyloxy, and the like. Lower alkoxy as the aforesaid substituent includes preferably methoxy, ethoxy, and the like.

"Cycloalkyl" refers to a monocyclic saturated carbocyclic ring of $C_3$ to $C_6$, wherein one carbocyclic ring carbon is the point of attachment. Examples of cycloalkyl include, but are not limited to, cyclopropyl, cyclobutyl, cyclopentyl, cyclohexyl, and the like.

"Cycloheteroalkyl" refers to a monocyclic saturated ring containing at least one heteroatom selected from N, S and O of $C_3$ to $C_6$, in which the point of attachment may be carbon or nitrogen. Examples of "cycloheteroalkyl" include, but are not limited to, pyrrolidinyl, piperidinyl, piperazinyl, imidazolidinyl, tetrahydrofuranyl, morpholinyl, and the like.

"Aryl" refers to a mono- or bicyclic aromatic rings containing only carbon atoms. The term also includes aryl group fused to a monocyclic cycloalkyl or monocyclic cycloheteroalkyl group in which the point of attachment is on the aromatic portion. Examples of aryl include phenyl, naphthyl, indanyl, indenyl, tetrahydronaphthyl, 2,3-dihydrobenzofuranyl, dihydrobenzopyranyl, 1,4-benzodioxanyl, and the like. The aryl ring may be unsubstituted or substituted on one or more carbon atoms.

"Heteroaryl" refers to a mono- or bicyclic aromatic ring, wherein each ring has 5 or 6 carbons, containing at least one heteroatom selected from N, O and S. Examples of heteroaryl include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzoxazolyl, benzothiazolyl, benzimidazolyl, benzofuranyl, benzothiophenyl, furo (2,3-b)pyridyl, quinolyl, indolyl, isoquinolyl, and the like. The heteroaryl ring may be unsubstituted or substituted on one or more carbon atoms.

As used herein, the term "anion" refers to a mono-anion or a di-anion.

The compounds in the processes of the present invention include stereoisomers, diastereomers and geometrical isomers, or tautomers depending on the mode of substitution. The compounds may contain one or more chiral centers and occur as racemates, racemic mixtures and as individual diastereomers, diastereomeric mixtures, enantiomeric mixtures or single enantiomers, or tautomers. The present invention is meant to comprehend all such isomeric forms of the compounds in the compositions of the present invention, and their mixtures. Therefore, where a compound is chiral, the separate enantiomers, and diastereomers, substantially free of the other, are included within the scope of the invention; further included are all mixtures of enantiomers, and all of the mixtures of diastereomers. Also included within the scope of the invention are salts, polymorphs, hydrates and solvates of the compounds and intermediates of the instant invention.

Compounds of the structural formula I and structural formula II include stereoisomers, such as the trans-form of compounds of the general formulas IA and IIA:

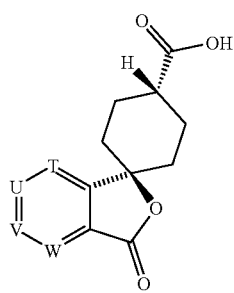

IA

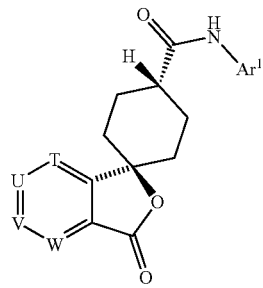

IIA and the cis-form compounds of the general formula IB and IIB:

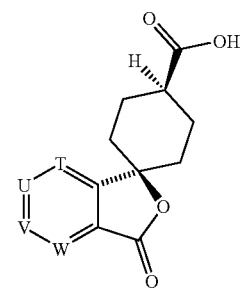

IB

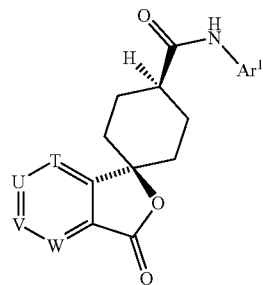

IIB

The trans-form is preferred.

The term "4-carboxylic acid substituted cyclohexanone" is defined as a 1-oxo-cyclohexanone substituted at the 4 position with a carboxylic acid. The term "4-carboxylic acid precursor substituted cyclohexanone" is defined as a 1-oxo-cyclohexanone substituted at the 4 position with a carboxylic acid precursor, such as an acid (—$CO_2H$), nitrile (—CN), alcohol (—$CH_2OH$), ester, ketal, or a protected carboxylic acid, such as an amide (i.e. —C(O)NHR$^3$, wherein R$^3$ is lower alkyl, or (—C(O)N(R$^3$)$_2$, wherein R$^3$ is lower alkyl), or a hydrazide (i.e. —C(O)NH$_2$NH$_2$), and the like.

For example, a 4-carboxylic acid precursor substituted cyclohexanone is a compound of formula IV

IV wherein R$^1$ is selected from the group consisting of:
(1) —$CO_2H$,
(2) —CN,
(3) —$CH_2OH$, (4) —CO$_2$R$^2$, wherein R$^2$ is selected from the group consisting of:
  (a) lower alkyl, and
  (b) —CH$_2$-phenyl, wherein the phenyl group is unsubstituted or substituted with a substituent selected from the group consisting of:
    (1) lower alkyl,
    (2) lower alkoxy, and
    (3) —NO$_2$,
(5) —C(O)NHR$^3$, wherein R$^3$ is lower alkyl,
(6) —C(O)N(R$^3$)$_2$, wherein R$^3$ is lower alkyl,
(7) —C(O)NH$_2$NH$_2$, and
(8) a ketal selected from the group consisting of

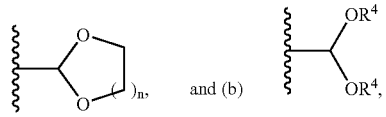

wherein n is 1 or 2, and R$^4$ is lower alkyl.

The term "protected carboxylic acid" refers to a carboxylic acid that is protected with a carboxylic acid protecting group readily known to one of ordinary skill in the art (See Protective Groups in Organic Synthesis, T. W. Greene, John Wiley & Sons, (1999)), such as amide protecting groups of the general formula —C(O)NHR$^3$ or —C(O)N(R$^3$)$_2$, or a hydrazide protecting groups of general formula —C(O)NH$_2$NH$_2$, and the like.

The conversion of the carboxylic acid protecting group into the free carboxylic acid may be carried out depending upon the kinds of the aforesaid protecting groups, for example, by the manner readily known to one of ordinary skill in the art of organic synthesis, (See Protective Groups in Organic Synthesis, T. W. Greene, John Wiley & Sons, (1999)). For example, conversion of an ester into a carboxylic acid may be carried out by solvolysis using acid, such as trifluoroacetic acid, formic acid, hydrochloric acid or the like, or base, such as potassium hydroxide, sodium hydroxide, lithium hydroxide, calcium hydroxide, or the like; chemical reduction using metallic complex hydride, or the like; or catalytic reduction using palladium-carbon catalyst, Raney nickel catalyst, or the like.

In general, the conversion of an amide, or hydrazide, of general formula —C(O)NHR$^3$, —C(O)N(R$^3$)$_2$, or —C(O)NH$_2$NH$_2$ to a carboxylic acid of formula —CO$_2$H may be carried out, for example, by acidic hydrolysis, or for example, by the manner described in the literature [Comprehensive Organic Transformations, R. C. LaRock, Wiley-VCH, (1999)], or for example, by the manner readily known to one of ordinary skill in the art of organic synthesis.

In general the conversion of an aryl, such as a phenyl group, to a carboxylic acid may be carried out by oxidation with ruthenium oxide as described in the literature [Tet. Lett., p. 4729 (1967); Chem. Comm. p. 1420 (1970)].

The conversion of the alcohol (—CH$_2$OH) into the free carboxylic acid, may be carried out by oxidation. The conversion of the nitrile (—CN) into the free carboxylic acid may be carried out by hydrolysis. For example, the conversions of the alcohol and the nitrile may be carried out by the manner described in the literature [Comprehensive Organic Transformations, R. C. LaRock, Wiley-VCH, (1999)], or by the manner readily known to one of ordinary skill in the art of organic synthesis.

The salts of compounds of formula I, IA, IB, and IC refer to the pharmaceutically acceptable and common salts, for example, base addition salt to carboxyl group when the compound has a carboxyl group, or acid addition salt to amino or basic heterocyclyl when the compound has an amino or basic heterocyclyl group, and the like.

The base addition salts include salts with alkali metals (including, but not limited to, sodium, potassium); alkaline earth metals (including, but not limited to, calcium, magnesium); ammonium or organic amines (including, but not limited to, trimethylamine, triethylamine, dicyclohexylamine, ethanolamine, diethanolamine, triethanolamine, procaine, N,N'-dibenzylethylenediamine), and the like.

The acid addition salts include salts with inorganic acids (including, but not limited to, hydrochloric acid, sulfuric acid, nitric acid, phosphoric acid, perchloric acid), organic acids (including, but not limited to, maleic acid, fumaric acid, tartaric acid, citric acid, ascorbic acid, trifluoroacetic acid, acetic acid), sulfonic acids (including, but not limited to, methanesulfonic acid, isethionic acid, benzenesulfonic acid, p-toluenesulfonic acid, p-toluenesulfonic acid monohydrate, p-toluene sulfonic acid hydrate, camphor sulfonic acid), and the like.

In the schemes and examples below, various reagent symbols and abbreviations have the following meanings:
AcOEt or EtOAc: ethyl acetate
n-BuLi or BuLi: n-butyl lithium
sec-BuLi: sec-butyl lithium
t-BuLi: tert-butyl lithium
CSA: camphor sulfonic acid
DBU: 1,8-Diazabicyclo[5.4.0]undec-7-ene
DMAC: N,N-dimethylacetamide
-Et: —CH$_2$CH$_3$
EtOH: ethanol
g: grams
IPAC: isopropyl acetate
HCl: hydrochloric acid
H$_2$SO$_4$: sulfuric acid
KHMDS: potassium hexamethyl disilazide
LiBr: lithium bromide
LiHMDS: lithium hexamethyl disilazide
LiTMP: lithium tetramethyl piperadide
NaCl: sodium chloride
NaHMDS: sodium hexamethyl
NaOEt: sodium ethoxide
mL: milliliter
mmol: millimole
mol: moles/liter
MTBE: methyl t-butyl ether
THF: tetrahydrofuran
TsOH: p-toluene sulfonic acid
TsOH.H$_2$O p-toluene sulfonic acid monohydrate The compounds of the present invention can be prepared by employing the general process in the General Scheme. The novel processes can be exemplified in Schemes 1 and 2, which illustrate the preparation of the spirolactone of structural formula I, IA, IB and IC, and salts thereof. The salts of IA and IB may be separated and individually reacted with an amine, H$_2$NAr$^1$. For example, the neutralization, activation and subsequent reaction of the salt of IA with H$_2$NAr$^1$ yields compounds of formula II.

The amide substituted phenyl, pyridine, pyrazine, and pyrimidine starting materials of general structure III and A, as shown in the General Scheme, Scheme 1 and Scheme 2, are either commercially available or readily accessible from commercially available starting materials.

The 4-R$^1$ substituted cyclohexanones of formula IV, in which the R$^1$ substituent is selected from an acid, a nitrile, an alcohol, a ketal, an ester, or a protected carboxylic acid, such as an amide or a hydrazide, are useful in the processes of this invention. The 4-$R^1$ substituted cyclohexanones of formula IV, in which the $R^1$ substituent is an ester, are particularly useful in Schemes 1 and 2. The 4-$R^1$ substituted cyclohexanone starting materials are either commercially available, such as ethyl-4-oxocyclohexanone carboxylate, or are readily accessible from commerically available starting materials. For example, other 4-substituted esters are readily accessible from ethyl-4-oxocyclohexane carboxylate via transesterification.

In scheme 1, the 4-$R^1$ substituted cyclohexanone is converted to the carboxylic acid before ring lactonization to form the spirolactone IC, via intermediate C, followed by separation into IA and IB. Compound IC is treated with an acid to form a mixture of the salts IA and IB, which may be separated to give the individual salts. Alternatively, compound IC is treated with an acid to form only the salt of IA, which may then be separated from the free acid IB. Alternatively, compound IC is treated with an acid to form only the salt of IB, which may then be separated from the free acid IA.

In Scheme 2, the ring lactonization, via intermediate D, to give the spirolactone E occurs prior to the conversion of the 4-$R^1$ substituted cyclohexanone into the 4-carboxylic acid substituted cyclohexanone IA and IB. Compound E may be treated with an acid to form salts of compound E (compounds F and G). Compounds F and G may be separated and individually treated with an acid or aqueous acid to form either compound IA from compound F, or compound IB from compound G. Alternatively, the mixture of compounds F and G may be treated with an acid or aqueous acid to form a mixture of compounds IA and IB.

GENERAL SCHEME

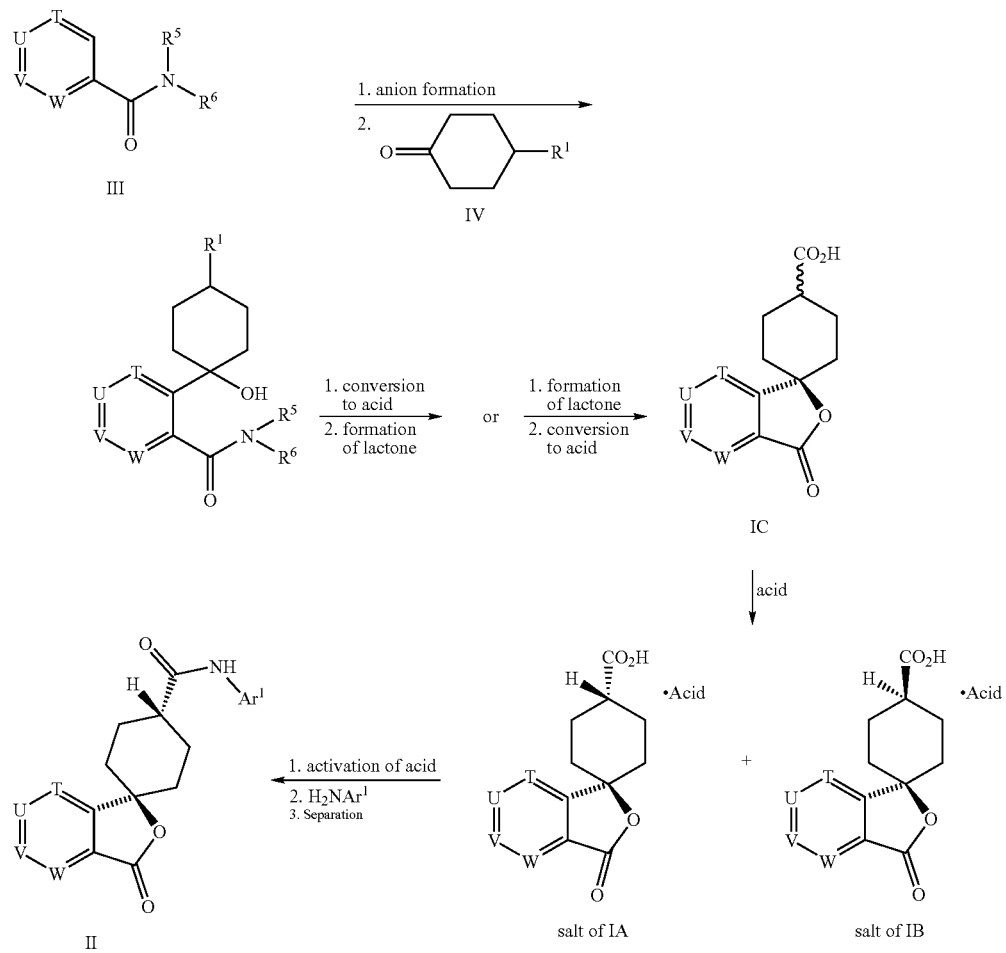

SCHEME 1

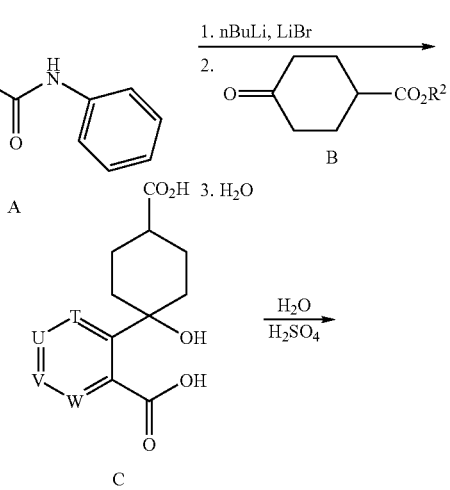

-continued
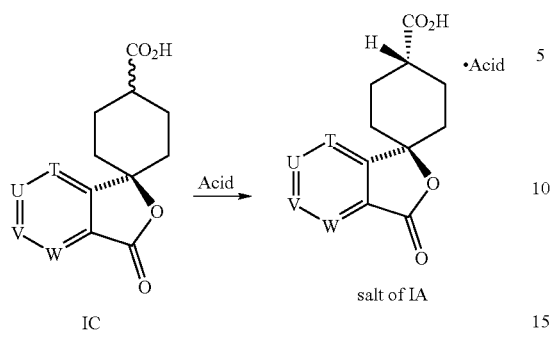
salt of IA
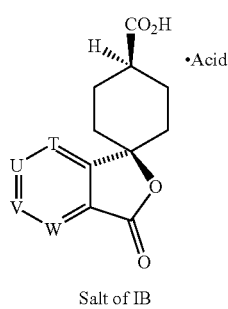
Salt of IB
SCHEME 2
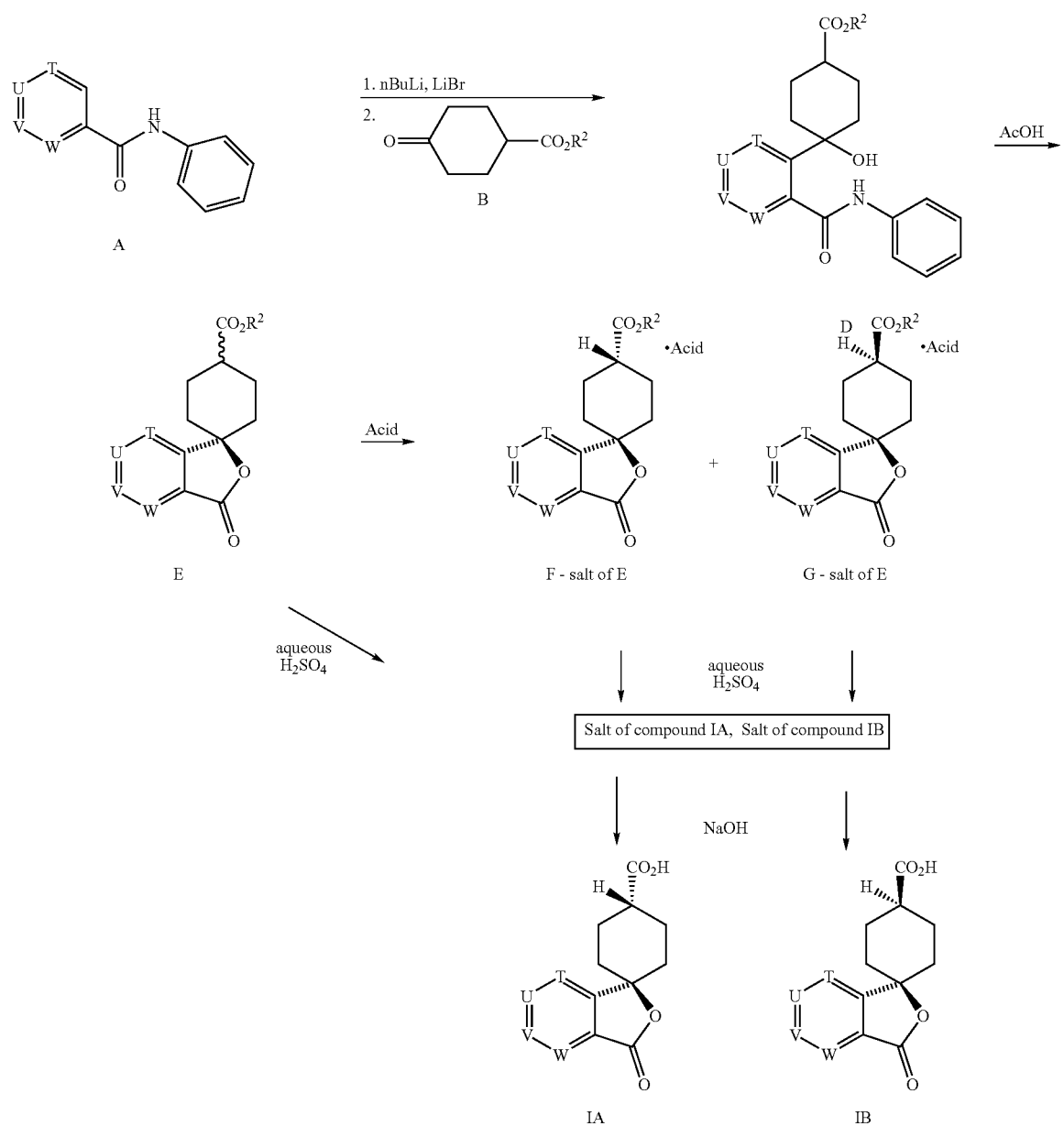

EXAMPLE 1

Preparation of Trans-1'-oxospiro[cyclohexane-1,3'(1'H)-furo[3,4-C]pyridine]-4-carboxylic acid, 1-5, (Method A)

Step A: Preparation of Compound 1-3

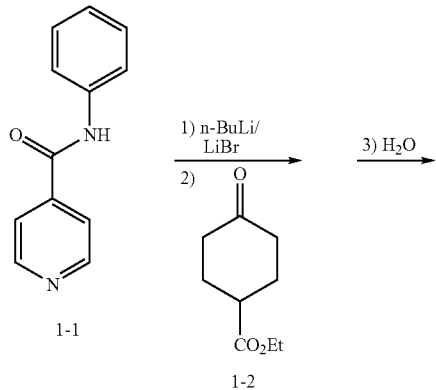

The isonicotinamide 1-1 (100 g, 0.50 mol, Kingchem), THF (0.5 L) and a 1 M LiBr solution (prepared by dissolving 1.50 mol of LiBr in 1.5 L of THF) were mixed in a flask. The resulting solution was degassed with nitrogen and cooled to −65° C. n-BuLi (1.56 M in hexane; 666 mL, 1.04 mol) was then added while maintaining the batch temperature below −55° C. The resulting solution was then aged at a temperature less than −55° C. for a period between 1 to 7 hours to give a metalated anilide mixture.

A solution of ethyl 4-oxocyclohexanecarboxylate 1-2 (100 mL, 0.63 mol, EMS Dottikon AG) in THF (1 L) was cooled in a separate flask to a temperature below −60° C. To the solution was added the above metalated anilide mixture, while maintaining the batch temperature below −55° C. The resulting solution was aged at a temperature below −55° C. for 1 hour and then carefully quenched into $H_2O$ (1 L). The resulting mixture was warmed to 40° C. and aged at 40° C. for a period between 1 to 4 hours. After cooling to room temperature, the organic layer was removed and the aqueous layer (1.3 L; pH~11) was washed with THF (1 L) to give an aqueous solution of the diacid 1-3.

Selected Signals: $^1$H NMR (500.13 MHz, DMSO-$d_6$): δ 8.55 (s, 1H), 8.48 (d, J=4.9 Hz, 1H), 7.27 (d, J=4.9 Hz, 1H). 2.58 (m, 1H), 1.77-1.95 (m, 8H).

Step B: Preparation of Compound 1-4

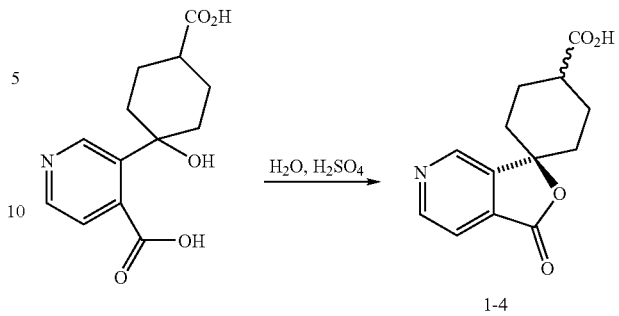

To the aqueous solution of the diacid 1-3 from Step A was added $H_2O$ (500 mL, 5 mL/g of anilide) and 47% aqueous $H_2SO_4$ to adjust to pH 2~3, maintaining the temperature below 30° C. The resulting white suspension was aged at a temperature of 30° C.-70° C. for a period of 1 to 4 hours. After cooling the batch, THF (2500 mL) and 20% aqueous NaCl (600 ml) were added to extract the product acid 1-4. After the separation of the two layers, the water layer was re-extracted with THF (1000 mL). The combined THF extracts (3500 mL) were concentrated to 1250 mL. The mixture turned to a suspension of product acid 1-4 during the distillation.

Selected Signals: $^1$H NMR (300.13 MHz, DMSO-$d_6$): δ 12.31 (br, 1H), 9.10 (d, 1H), 8.85 (m, 1H), 7.82 (m, 1H). 2.70 (m, 0.45H), 2.43 (m, 0.55H), 1.65-2.25 (m, 8H), Step C: Separation of Compound 1-4 into Compounds 1-5 and 1-6

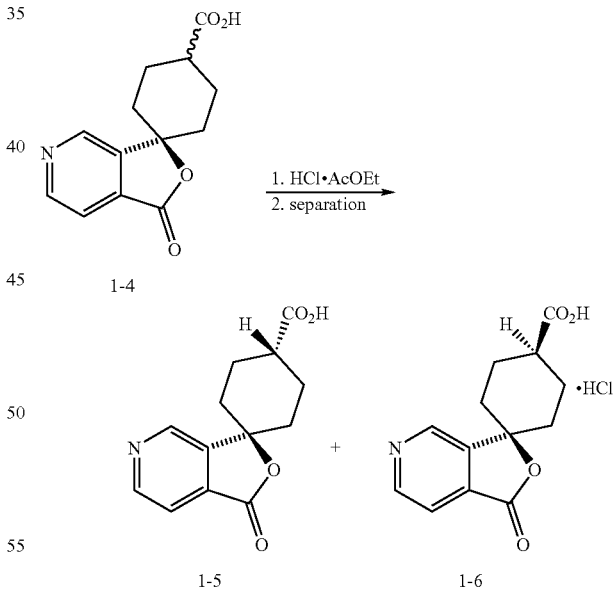

To the suspension of product acid 1-4 was added 3.3 M HCl-AcOEt at room temperature, and the mixture was then aged at a temperature between about 40° C.-60° C. for a period of about 24 to 48 hours. The batch was filtered at room temperature and the filter cake was washed with THF (2×100 mL). The combined filtrate and washings were concentrated to 800 mL under reduced pressure at a temperature of 20° C.-60° C. DMF (80 mL, 2 mL/g to trans acid assay) and $H_2O$ (80 mL) were added, and the mixture was concentrated to 160 mL (4 mL/g to trans acid assay) by vacuum distillation at 20° C. to 60° C. giving slightly brownish suspension.

To the suspension was added H₂O (800 mL, 20 mL/g to trans acid assay), and the resulting mixture was then aged at room temperature for a period of 0.5-5 hours. The batch was filtered, washed with H₂O (2×80 mL, 2 mL/g to trans acid assay), and dried at 20° C.-60° C. to afford the acid product 1-5.

Selected Signals: $^1$H NMR (300 MHz, DMSO-d$_6$): δ 1.76-1.85 (m, 2H), 1.90-2.11 (m, 6H), 2.68-2.74 (m, 1H), 7.84 (dd, 1H, J=1.0, 5.0 Hz), 8.87 (d, 1H, J=5.0 Hz), 9.06 (d, 1H, j=1.0 Hz), 12.35 (brs, 1H).

EXAMPLE 2

Preparation of Trans-1'-oxospiro[cyclohexane-1,3' (1'H)-furo[3,4-C]pyridine]-4-carboxylic acid, 2-5, (Method B)

Step A: Preparation of Compound 2-3

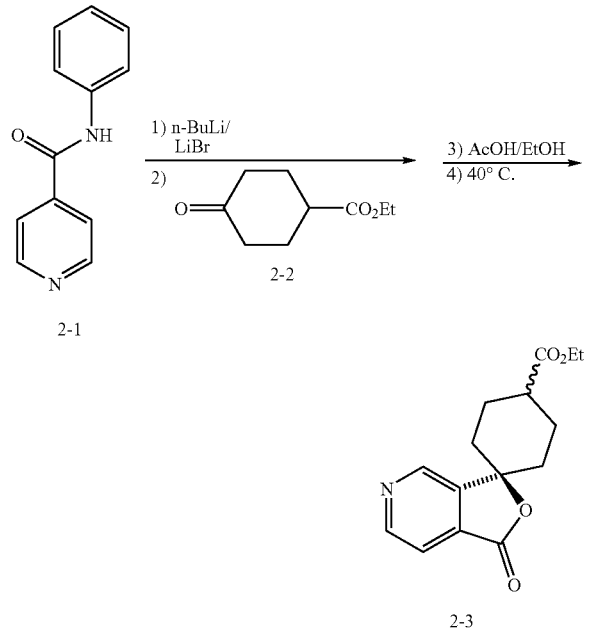

The isonicotinamide 2-1 (100 g, 0.50 mol, Kingchem), THF (0.5 L) and a 1 M LiBr solution (prepared by dissolving 1.50 mol of LiBr in 1.5 L of THF) were mixed in a flask. The resulting solution was degassed with nitrogen and cooled to less than −65° C. n-BuLi (1.56 M in hexane; 666 mL, 1.04 mol) was then added while maintaining the batch temperature below −55° C. The resulting solution was then aged at a temperature less than −55° C. for a period of 1 to 12 hours to give a metalated anilide mixture.

A solution of ethyl 4-oxocyclohexanecarboxylate 2-2 (100 mL, 0.63 mol, EMS Dottikon AG) in THF (89 g in 1 L) was cooled in a separate flask to a temperature below −60° C. To the solution was added the above metalated anilide mixture, while maintaining the batch temperature below −55° C. The resulting solution was aged at a temperature below −55° C. for 1 hour and then carefully quenched with ethanol and acetic acid (320 ml; 10:3.5 ethanol/acetic acid). The solution was then warmed to 40° C. and aged for 1 to 6 hours to give a solution of spirolactone 2-3.

Selected Signals: $^1$H NMR (400.13 MHz; CDCl$_3$): δ 9.00 (d, J=1.0 Hz, 1H), 8.85 (d, J=5.0 Hz, 1H), 7.75 (dd, J=5.0 Hz, 1.0 Hz, 1H), 4.22 (q, J=7.0 Hz, 2H), 2.79 (br m, 1H), 2.22-2.10 (overlapping m, 6H), 1.84-1.74 (overlapping m, 2H), 1.31 (t, J=7.0 Hz, 3H).

Selected Signals: $^{13}$C NMR (100.62 MHz; CDCl$_3$): 174.5, 167.9, 150.2, 147.6, 133.2, 118.9, 86.6, 60.5, 38.0, 33.0, 23.6, 14.2.

Step B: Preparation of Compound 2-4

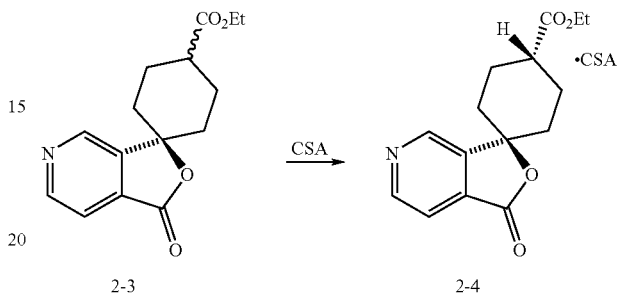

The solvent of the solution of spirolactone 2-3 from Step A was switched into EtOAc by distillation. The EtOAc solution was washed with aqueous HCl (2×500 mL), and then washed with aqueous bicarbonate (250 mL). Camphorsulfonic acid (1 equivalent) in THF was added to the ethyl acetate solution and the mixture was stirred for 1 to 18 hours and then filtered to provide the desired spirolactone CSA salt 2-4.

Selected Signals: $^1$H-NMR (500.13 MHz; CDCl$_3$) δ: 9.26 (s, 1H), 9.17 (d, J=5.4 Hz, 1H), 8.19 (d, J=5.4 Hz, 1H), 4.25 (q, J=7.1 Hz, 2H), 3.39 (d, J=14.7 Hz, 1H), 2.99 (d, J=14.7 Hz, 1H), 2.83 (quintuplet, J=4.0 Hz, 1H), 2.51 (ddd, J=3.9, 11.5, 15.0 Hz, 1H), 2.38 (dt, J=3.4, 18.5 Hz, 1H), 2.23-2.29 (m, 4H), 2.12-2.18 (m, 2H), 2.11 (t, J=4.4 Hz, 1H), 2.01-2.09 (m, 1H), 1.94 (d, J=18.5 Hz, 1H), 1.93 (dt, J=4.9, 10.5 Hz, 1H), 1.81-1.85 (m, 2H), 1.44 (ddd, J=3.9, 9.4, 12.7 Hz, 1H), 1.33 (t, J=7.1 Hz, 3H), 1.07 (s, 3H), 0.87 (s, 3H).

Step C: Preparation of Compound 2-5

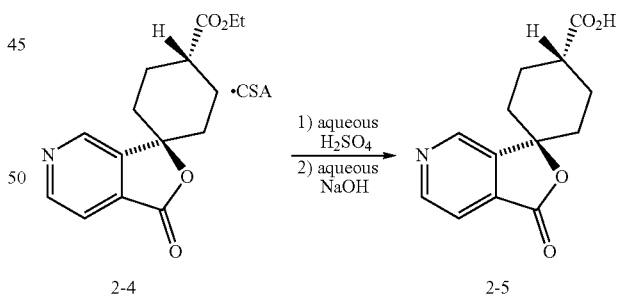

The spirolactone CSA salt 2-4 was dissolved in aqueous sulfuric acid and warmed to 50° C. to 90° C. for 0.5 to 12 hours. The reaction was cooled to a temperature of 15° C. to 30° C. and the pH was adjusted with sodium hydroxide to pH 2 to 4. The resulting slurry was aged for 0.5 to 15 hours and filtered to yield the desired acid 2-5.

Selected Signals: $^1$H NMR (400.13 MHz; DMSO-d$_6$): δ 12.34 (br, 1H), 9.04 (d, J=1.0 Hz, 1H), 8.85 (d, J=5.0 Hz, 1H), 7.82 (dd, J=5.0 Hz, 1.0 Hz, 1H), 2.70 (br m, 1H), 2.08-1.89 (overlapping m, 6H), 1.82-1.76 (overlapping m, 2H).

Selected Signals: $^{13}C$ NMR (100.62 MHz; DMSO-$d_6$): 175.9, 167.9, 150.6, 147.5, 144.9, 133.1, 119.1, 87.2, 38.1, 33.1, 23.9.

What is claimed is:

1. A process for preparing a compound of the formula IC, or a salt thereof,

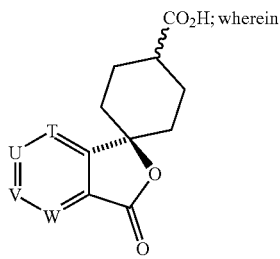

IC

T, U, V and W are each independently selected from the group consisting of
   (1) nitrogen, and
   (2) methine,
   wherein the methine group is unsubstituted or optionally substituted with a substituent selected from the group consisting of
      (a) halogen,
      (b) lower alkyl,
      (c) hydroxy, and
      (d) lower alkoxy, and
   wherein at least two of T, U, V, and W are methine;
comprising the steps of
(a) combining a strong base with a compound of formula A

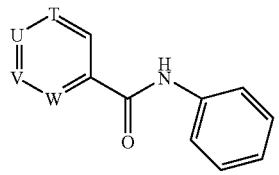

A in an aprotic solvent to form a solution;
(b) reacting a compound of formula B

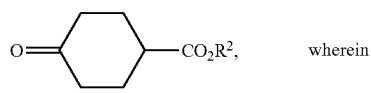

B wherein $R^2$ is selected from the group consisting of:
   (a) lower alkyl, and
   (b) —$CH_2$-phenyl, wherein the phenyl group is unsubstituted or substituted with a substituent selected from the group consisting of
      (1) lower alkyl,
      (2) lower alkoxy, and
      (3) —$NO_2$,
with the solution of step (a) to form a solution;
(c) reacting the solution of step (b) with water to form a solution; and
(d) adjusting the pH of the solution of step (c) to between about 0 and 4 with an acid to afford the compound IC, or a salt thereof.

2. The process of claim 1 further comprising the step (e) of isolating the compound of formula IC, or a salt thereof.

3. The process of claim 1 wherein the aprotic solvent of step (a) is selected from the group consisting of tetrahydrofuran, toluene, heptane, dimethoxyethane, benzene, and hexane, diethyl ether, xylene, or a mixture thereof.

4. The process of claim 1 wherein the strong base of step (a) is selected from the group consisting of n-BuLi, sec-BuLi, t-BuLi, LiHMDS, NaHMDS, KHMDS and LiTMP.

5. The process of claim 1 wherein step (a) further comprises adding a salt selected from the group consisting of LiBr, LiCl, LiI, $LiBF_4$, $LiClO_4$, and $CeCl_3$.

6. The process of claim 1 wherein $R^2$ is selected from the group consisting of —$CH_3$, —$CH_2CH_3$, —$(CH_2)_2CH_3$, —$CH(CH_3)_2$, —$(CH_2)_3CH_3$, and —$CH(CH_3)_3$.

7. The process of claim 1 wherein the acid of step (d) is selected from the group consisting of hydrochloric acid, sulfuric acid, methane sulfonic acid, trifluoromethane sulfonic acid, and or a mixture thereof.

8. The process of claim 1 wherein T, V and W are methine, wherein the methine group is unsubstituted or optionally substituted with a substituent selected from the group consisting of
   (a) halogen,
   (b) lower alkyl,
   (c) hydroxy, and
   (d) lower alkoxy; and
U is nitrogen.

9. The process of claim 1 wherein T, V and W are unsubstituted methine; and U is nitrogen.

10. The process of claim 1 wherein T, U, V and W are methine, wherein the methine group is unsubstituted or optionally substituted with a substituent selected from the group consisting of
   (a) halogen,
   (b) lower alkyl,
   (c) hydroxy, and
   (d) lower alkoxy.

* * * * *